(12) United States Patent
Greco

(10) Patent No.: US 9,521,976 B2
(45) Date of Patent: Dec. 20, 2016

(54) METHOD AND APPARATUS FOR ENCOURAGING PHYSIOLOGICAL CHANGE THROUGH PHYSIOLOGICAL CONTROL OF WEARABLE AUDITORY AND VISUAL INTERRUPTION DEVICE

(71) Applicant: Devon Greco, Bend, OR (US)

(72) Inventor: Devon Greco, Bend, OR (US)

( * ) Notice: Subject to any disclaimer, the term of this patent is extended or adjusted under 35 U.S.C. 154(b) by 251 days.

(21) Appl. No.: 14/163,971

(22) Filed: Jan. 24, 2014

(65) Prior Publication Data

US 2014/0336473 A1 Nov. 13, 2014

Related U.S. Application Data

(60) Provisional application No. 61/756,450, filed on Jan. 24, 2013, provisional application No. 61/918,644, filed on Dec. 19, 2013.

(51) Int. Cl.

| | |
|---|---|
| *A61B 5/02* | (2006.01) |
| *A61B 5/00* | (2006.01) |
| *A61B 5/0205* | (2006.01) |
| *A61B 5/0476* | (2006.01) |
| *A61B 5/0488* | (2006.01) |

(Continued)

(52) U.S. Cl.
CPC ........... *A61B 5/486* (2013.01); *A61B 5/02055* (2013.01); *A61B 5/0402* (2013.01); *A61B 5/04004* (2013.01); *A61B 5/0476* (2013.01); *A61B 5/0482* (2013.01); *A61B 5/0488* (2013.01); *A61B 5/6803* (2013.01); *A61B 5/7225* (2013.01); *A61B 5/742* (2013.01); *A61B 5/7445* (2013.01); *A61B 5/024* (2013.01); *A61B 5/053* (2013.01); *A61B 5/7405* (2013.01); *A61B 5/7455* (2013.01)

(58) Field of Classification Search
None
See application file for complete search history.

(56) References Cited

U.S. PATENT DOCUMENTS 6,167,298 A   12/2000 Levin
6,456,438 B1   9/2002 Lee et al.
(Continued)

*Primary Examiner* — Brian T Gedeon
*Assistant Examiner* — Ankit D Tejani
(74) *Attorney, Agent, or Firm* — Bacon & Thomas, PLLC

(57) ABSTRACT

A biofeedback system and method enables biofeedback training to be accomplished during normal interaction by an individual with the individual's environment, for example while reading, playing video games, watching TV, participating in sports activities, or at work. Physiologic data is processed and used to generate one or more control signals based on the physiologic data. The control signals may be proportional to a result of the data processing, or based on comparison of the processing results with at least one fixed or adaptive threshold. The control signal is supplied to a wearable device through which the individual receives sensory information from the individual's environment, and serves to interrupt or modify the sensory information. The wearable device may be an eyeglass device including a dynamic lens display, with the control signal being supplied to the dynamic lens display to modulate visual information received through the eyeglass device by obscuring, distorting, or otherwise affecting the clarity of the visual information. Feedback may also be provided in the form of auditory or tactile feedback.

51 Claims, 10 Drawing Sheets

(51) Int. Cl.
*A61B 5/0402* (2006.01)
*A61B 5/04* (2006.01)
*A61B 5/0482* (2006.01)
A61B 5/024 (2006.01)
A61B 5/053 (2006.01)

(56) References Cited

U.S. PATENT DOCUMENTS

| | | | |
|---|---|---|---|
| 2008/0102424 A1* | 5/2008 | Holljes | A63B 21/4047 434/247 |
| 2008/0161673 A1* | 7/2008 | Goodall | A61B 5/04001 600/409 |
| 2008/0281221 A1 | 11/2008 | Greco et al. | |
| 2009/0318826 A1* | 12/2009 | Green | A61B 5/048 600/545 |
| 2010/0121158 A1* | 5/2010 | Quevedo | A61B 5/0482 600/301 |
| 2010/0280338 A1* | 11/2010 | Chou | A61B 5/6838 600/301 |
| 2012/0004034 A1* | 1/2012 | Pope | A63F 13/06 463/36 |
| 2014/0023999 A1 | 1/2014 | Greder | |

* cited by examiner

METHOD AND APPARATUS FOR ENCOURAGING PHYSIOLOGICAL CHANGE THROUGH PHYSIOLOGICAL CONTROL OF WEARABLE AUDITORY AND VISUAL INTERRUPTION DEVICE

This application claims the benefit of U.S. Provisional Appl. Ser. Nos. 61/756,450, filed Jan. 24, 2013, and 61/918,644, filed Dec. 19, 2013, each of which is incorporated by reference herein.

BACKGROUND OF THE INVENTION

1. Field of the Invention

The invention generally relates to the field of biofeedback. More particularly, the invention relates to a system and method for encouraging physiologic (also known as physiological) self-regulation based on visual, auditory, and/or tactile feedback of measured and processed physiologic data.

The system and method of the invention enables biofeedback or neurofeedback (a type of biofeedback) to be carried out during normal everyday tasks such as, by way of example and not limitation, reading, listening to instructions, watching a movie, driving a vehicle, and involvement in sports activities. This is accomplished by using a wearable device that does not interfere with the everyday activities and that does not require a secondary feedback device, such as an external computer display, to provide the stimulation that prompts the physiologic response. According to the present invention, the stimulation that prompts the initial physiologic response is provided by the user's or subject's environment, and the physiologic response-based feedback is used to modify the environmental stimulus, for example by restricting or modifying the user's view of the environment. Additional visual, aural, or tactile feedback may be provided but the primary stimulus is the user's natural or ordinary environment and not a manufactured stimulus such as a game program or other stimulus providing computer display.

The physiologic data may include, again by way of example and not limitation, data relating to heart rate, galvanic-skin response, body temperature, blood pressure, electroencephalography (EEG), electromyography (EMG), or any other normally-involuntary physiologic function or measure that a user can be taught to consciously control in response biofeedback or neurofeedback.

In a preferred embodiment, the biofeedback modulates the amount of light passing through the wearable device, thereby changing the user's view of his or her environment. In addition, the system and method of the invention may utilize complimental tactile feedback, which may take the form of vibrations, and/or aural feedback. However, the invention is not limited to modulation of the amount of light passing through the wearable device as the primary stimulus, but rather encompasses any effects that inhibit or change the way the user senses his or her environment, such as brightness tinting, blocking, fuzzing, fading, muting, or overlaying of external visual, auditory, or tactile feedback.

2. Description of Related Art

The terms biofeedback and neurofeedback refer to techniques and in which an individual learns to consciously control involuntary responses such as heart rate, blood pressure, brain waves, anxiety, and muscle tension with the help of man-machine interfaces such as computer screens and/or other devices that generate visual, auditory, and/or tactile feedback of the physiologic data and thereby provide information concerning the involuntary response that the individual would normally be unable to consciously detect in the absence of the man-machine interface.

In conventional biofeedback and neurofeedback systems, the information concerning the involuntary response, or normally unconscious physiologic processes, is conveyed back to the individual in the form of auditory and/or visual indicators such as beeps or graphs displayed on computer screen.

Biofeedback or neurofeedback systems can be used for a number of applications, such as to treat developmental and behavioral disorders like attention deficit hyperactivity disorder (ADHD), learning disabilities, cognitive effects of aging and other cognitive disorders. People with these disorders have severe difficulty efficiently processing information, controlling body impulses, focusing, and maintaining attention. Characteristically, those suffering from these disorders can display inattentiveness, impulsiveness, and hyperactivity. These disorders often lead to learning and behavior problems at home, school or work. Generally, biofeedback systems can be used to address cognitive processing disorder, learning disability, anxiety, depression, mild closed head injury and cognitive effects of aging and the like as these can respond favorably to treatment using biofeedback and, more specifically, neurofeedback.

Treatments for such disorders currently employ a variety of methods, including the use of medication, behavioral therapy, audio-visual entrainment, cerebella function stimulation and brainwave biofeedback training, to reduce the symptoms. Biofeedback and neurofeedback training uses machines to measure and display body functions and states such as heart rate, blood pressure, skin temperature, muscle tension, brain activity, electroencephalograph (EEG), electromyograph (EMG), and skin conductance. The patient can monitor these body functions and see how and why the body functions change through stages of high and low degrees of activity, with the goal that the patient eventually learns to self-regulate and control those body functions.

Biofeedback and neurofeedback training allows the patient to monitor and improve his/her physiology by observing the machine that measures and displays their body functions, making the patient aware of the activities which promote improvement, thus reinforcing the patient's ability to self-regulate and control the body functions. This is especially critical in today's technologically advanced work environments, where increased stress, high demand for multitasking, lack of awareness, poor attention and the cognitive effects of aging greatly influence productivity and errors in work performance. However, conventional biofeedback and neurofeedback training are conventionally conducted in a clinical setting or in front of a specially equipped personal computer system, rather than in a work environment or other setting under conditions that trigger behavioral or physiologic conditions that need to be corrected.

Although traditional biofeedback and neurofeedback systems and methods influence changes in physiology to improve inefficient behaviors, there is little opportunity to use the self-regulation training in an environment in which the behavior is exhibited, and therefore little opportunity to create a direct cognitive connection between the ineffective behavior, the immediate task at hand, and the response of the self-regulation training. This lack of a direct cognitive connection results in a waste of a true teachable opportunity.

Technologies known in the biofeedback art include methods for improving attention skill by rewarding specific brain signal patterns with desirable results such as success at playing a video game or altering the characteristics of the display of a video feed in a desirable manner. In one representation, the player or viewer is required to exhibit the required brain signal patterns that accompany normal cognition or behavior in order to win the video game or alter a simple computer animation desirably, as opposed to exhibiting cognitive states and behavior consistent with someone suffering from ADD or ADHD. Once the player or viewer exhibits the required brain signal patterns, the video game or computer generated animation becomes easier to play or advances or the viewer is rewarded with some type of visual or auditory reinforcement primary to the biofeedback training and not related to the external environment. A measurement system senses the EEG signals from the player and routes them to the computer where the video game difficulty is computed or the video feed characteristics are determined, therefore varying the difficulty of the video game or viewability of the video feed.

The known technologies that use video feeds such as DVD movies have the disadvantage of requiring extensive equipment, typically requiring a personal computer (PC) that is interfaced with video playback systems such as PC media players or external DVI) players and that feed the brain-activity-mediated signal to the PC screen or a television display. This requirement of a PC causes significant compatibility problems in an end user setup, often due to the varied versions and types of audio and video Coders/Decoders (CODECS) present on such systems. A PC mediated system also complicates the use of the training system for end users, and especially for the elderly. All known biofeedback and/or neurofeedback systems involve an active feedback mechanism that requires the user to actively engage in a specific process focusing on a computer or machine or other unnatural stimuli to receive biofeedback and/or neurofeedback. This is problematic because the user is required to engage in an activity he might otherwise not do in his daily life which makes it more difficult for the biofeedback benefits to transfer into daily life. There are individuals with extreme cognitive disorders such as post-concussion syndrome, or with congenital disorders, who are not able to receive the benefits of biofeedback because of their inability to focus on or understand a particular task or specific stimuli for any period of time. Paying attention to a computer display of a brain activity graph or animation for 15 to 30 minutes is beyond the scope of these individuals' ability and understanding.

The biofeedback systems and methods described in the art do not allow the user to receive biofeedback while doing normal daily activities, or are not effective for those with extreme cognitive disorders. In contrast, the present invention enables a user to receive biofeedback while interacting in daily activities like watching television, reading a book, or during a sports activity, by using the wearable device to create a changeable representation of the perceived environment based on physiologic activity to reinforce positive physiologic changes. For example, while engaged in a normal activity, the wearable device can create a visual or auditory feedback overlay reducing vision and/or hearing, impairing the individual's ability to interact with the task at hand.

In summary, the shortfalls of biofeedback in practice and prior art include utilization of a feedback/reinforcement mechanism to change physiology that is not directly representative of the user's actual environment and/or that are beyond the ability of severely impaired individuals. Traditional methods rely on visual and auditory representation of physiology through a computer or machine and reinforcement of the signal. The process of training is directed to the training activity itself in the hope that the reinforced changes transfer to the day-to-day environment. On the other hand, in the present invention, the process of training is directed to activities that occur in the day-to-day environment, rather than to the training activity itself.

SUMMARY OF THE INVENTION

It is accordingly an objective of the invention to provide a biofeedback system and method that addresses the shortcomings of the prior art by enabling biofeedback training to be accomplished during normal interaction with the user's or subject's environment. Because the training is direct and not one step removed from the environment, the transfer of learned skills is ensured.

To accomplish this objective, the present invention provides a method and system of transforming physiologic information obtained from biomedical instruments in order to use that information to modulate sound, sight, and tactile stimulation received by the user from the user's environment during normal interaction with that environment. The phrase "normal interaction with the environment" refers to interaction that would occur, or be carried out by the user, even in the absence of the biofeedback system and method.

Examples of activities that may be performed while using the method and system of the invention include:

Driving—While either learning to drive or becoming a better driver using driving simulators, the present invention provides visual, auditory and tactile feedback of cognitive performance to include: attention to the task, visual perception of distance to other objects, and impulsive responses to outside movement of things and other drivers and the response time to the driving experience.

Writing—While either typing on a keyboard or handwriting, the present invention provides visual, auditory and tactile feedback of cognitive performance to include: attention to the flow of sentence structure, grammatical and spelling accuracy, transferring thought into the written word, distraction in completing the written task and overall efficiency to the task.

Reading—While reading, the present invention provides visual, auditory and tactile feedback of cognitive performance to include: speed in which reading material is cognitively absorbed, recall and memory of reading material and accuracy in the processing of the read material and overall efficiency to the task.

Relaxing—While attempting to relax, the present invention provides visual, auditory and tactile feedback of the degree of relaxed mind and body state to include: the ability to reach a physical relaxed state, the amount of muscle tension throughout the body and feelings of anxiety, mind racing and a meditating state.

Watching television and/or any visual medium—While attempting to watch visual medium, the present invention provides visual, auditory and tactile feedback of cognitive performance to include: attention to the task, memory and recall to the observed information and ability to connect the discreet portions of the content together in a meaningful way.

In accordance with at least one embodiment of the present invention, the disclosed apparatus and methods can be used for safety, health, or productivity purposes. In one embodiment of the invention, physiologic signals related to stress, workload, or mental engagement could be used to control the lens opacity worn by a worker connected to the system.

In one scenario, a worker's physiologic signals may indicate he or she is mentally fatigued, anxious, drowsy, stressed, distracted, or otherwise not mentally engaged in a task, which would trigger the lens to become opaque, therefore inhibiting the worker from performing the task and indicating that one or more of the physiologic signals are not meeting the programmed criterion. Tactile vibration could also be generated to alert the worker that one or more physiologic signals are not meeting the programmed criterion. An aural reward feedback may also be generated to provide the worker an auditory indication of physiologic performance based on the programmed criterion.

Those skilled in the art will appreciate that feedback mechanisms that modulate or affect perception of the user's environment during the specific task in which the physiologic response is to be modified, for example by modulating lens opacity or amount of light that passes through the lens to a person's eyes while carrying out an activity such as driving or sports, makes the reinforcing feedback implicit in the task by inhibiting the person's ability to perceive the task at hand as well as explicit in the form of direct feedback (varying shades of tint through lens, tactile vibration, aural reward). In this way, there are several levels of reinforcement for subtle and non-subtle conditioning of the desirable physiologic response(s). The implications of a feedback system that is both explicit in the form of direct feedback, as well as implicit in the task, result in a noticeable change in stimulation and/or the person's environment, as well as inhibiting the user from performing a specific task by not being able to receive information necessary to effectively perform the task. In addition, the implicit nature of the feedback allows the reinforcement methods of conditioning to reach individuals who previously could not be affected by explicit feedback mechanisms due to a cognitive or other disorder. The inherent features related to the combination of an implicit and explicit feedback mechanism also enhances the effectiveness of the conditioning process in average individuals.

Different embodiments of the present invention are possible, and the components of the invention can vary depending upon implementation. For example, the invention may be used with either or both of a mobile device (such as smartphone/tablet ANDROID™, IPAD™/IPHONE™) or a personal computer to provide a convenient user interface and access to training protocols. Additionally, one or more of a wide variety of different measured physiologic signals can be used in accordance with the present invention, including but not limited to: EEGs, ECGs, EMG, skin temperature, skin conductance, heart rate, and/or event-related potentials (ERPs).

In one preferred embodiment of the present invention, a biofeedback system and method determines an individual's EEG index of attention, which can be used to assess his or her mental engagement at the task. Such assessment of mental engagement based on an EEG index of attention is disclosed in U.S. Pat. No. 5,377,100, issued on Dec. 27, 1994 to Pope et al., and incorporated herein by reference.

The present invention fully integrates biofeedback training into real life scenarios and allows for training control of physiologic signals for specific activities or performances. It offers a new generation of physiologic training technology that brings both explicit and implicit forms of feedback into the trainee's senses. Current systems typically deliver biofeedback in bland, minimally motivating task formats with direct feedback. The present invention's immersive feedback motivates trainees to participate in and adhere to the training process through the rewards inherent in controlling the senses and stimulation and without the demand, monotony or frustration potential of direct concentration on physiologic signals.

In exemplary embodiments of the invention described in detail herein, the system and method modifies the user's perception of his or her environment by modulating the amount of light allowed to pass through a head-worn eyeglass with a wired or wireless connection, through the intensity of tactile vibration placed on a user-worn device, and/or through aural reward feedback in proportion to the strength of a measured physiologic signal or signals, or by comparison of the signal(s) with a fixed or adaptive threshold. By basing the stimulation on the physiologic signal(s), the user is encouraged to change the physiologic signal(s) according to a programmed criterion, for example to increase, decrease, or maintain the signal(s), in order to modulate the stimulation in the desired direction, so as to produce a "reward" or to not produce a "penalty."

In the example of a head-worn eyeglass, the eyeglass contains at least one dynamic lens that are electronically controlled to affect the amount of light that passes through the lens, and/or to affect the clarity, obscurity, or distortion of an image by manipulating of the light that passes through the lens. In a preferred implementation, the dynamic lens is composed of a liquid crystal which blocks light passing through the lens when electrified. The lens is similar to the type used in active three-dimensional television glasses, which in the case of the television, are electrified at a very fast and alternating rate that produces a polarizing effect to cause the perception of a stereoscopic image. In the present invention, the lenses may be electrified at varying intensities to produce different levels of opacity.

According to another aspect of the invention, usable in connection with any of the above-mentioned embodiments involving different feedback devices, a reward is produced if the physiologic signals match the criterion set forth by a training protocol. The criterion may be, by way of example and not limitation, increasing skin temperature, increasing the amplitude of a Beta2 (12-20 Hz) EEG, or a decrease in heart rate. The training protocol can include increasing one or more physiologic signals and/or decreasing one or more other physiologic signals, and may take the form of a training "ratio" protocol in which positive feedback is generated based on increasing the magnitude of certain physiologic signal or signals while at the same time also generating positive feedback based on decreasing the magnitude of another separate physiologic signal or signals.

An exemplary training ratio algorithm uses EEG bandwidths as the controlling physiologic signal to control a reward based on the magnitudes of the EEG bandwidths $[(f1+f2)/(f3+f4)]$, where f1, f2, f3, f4, are EEG bandwidths. According to this algorithm, if the magnitudes of f1 and/or f2 (on the numerator of the training ratio) increase, a reward is generated and if the magnitudes of f1 and/or f2 decrease or no longer increase, a penalty is generated. On the other hand, according to this algorithm, if the magnitudes of f3 and/or f4 (on the denominator of the training ratio) decrease, a reward is generated and if the magnitudes of f3 and/or f4 increase or are no longer decreasing, a penalty is generated.

When applied to a dynamic lens device, the reward may be that the lens becomes clearer, allowing the user to look through the lens to better see his or her environment, which is interpreted by the user as a reward for his or her physiologic signals meeting the programmed criterion. The visual reward may be supplemented by an aural reward in the form of a positive and pleasing note or melody, a chime, a chord, a tone, or a tick, received by the user via an internal audio system and speaker of a mobile device, or via headphones worn by the user and connected to the mobile device. Conversely, a penalty may equate to the lens becoming darker or less clear, inhibiting the user from looking through the lens to see his or her environment. The penalty might also include the non-occurrence of a positive aural reward, and/or the occurrence of a negative aural penalty. The negative aural penalty might be a negative and displeasing noise such as a loud or high-pitch noise or chirp, a honk, a deep or low tone, or other displeasing sound audible to the human ear. Alternatively, by way of example and not limitation, the reward may also equate to the non-occurrence of a tactile vibration (caused for example by a coin vibrator motor placed in a band and worn around the wrist or ankle of the user), and/or the non-occurrence of a negative aural penalty, while the penalty may equate to the occurrence of tactile vibration felt by the user and interpreted as a penalty for his or her physiologic signals not meeting the programmed criterion, and/or the presence of a negative aural award.

In another embodiment of the invention, the programmed criterion which generates the feedback may be composed of a static threshold or thresholds in which only a certain magnitude level of a specified physiologic signal triggers the reward or penalty. For example, in the example of EEG bandwidth as the physiologic signal, the threshold to produce a reward may be a Beta2 (12-20 Hz) of at least 15 uV.

In yet another embodiment, an adaptive feedback system may be employed in which thresholds for feedback are set dynamically by the software and are affected by user performance. In an adaptive feedback system, the feedback difficulty is in proportion to user performance, such that when user performance improves, thresholds for rewards are increased to make it more difficult for the user to receive a reward, and such that when user performance declines, the thresholds for penalties are decreased to make it easier for the user to receive a reward or to not receive a penalty.

One type of adaptive feedback system that may be employed is known as a fuzzy logic feedback system has been employed. The fuzzy logic feedback system enables several input parameters, such as rate of change, deviation from expected level, and previously achieved performance, to be related to the output.

It should be understood by those skilled in the art that the descriptions and illustrations herein are by way of examples and the invention, or inventions, are not limited to the exact details shown and described. It is also to be understood that the invention(s) is in no way intended to be limited to the specific embodiments included in the following description and illustrated in the drawings, and the illustrated embodiments are capable of numerous modifications within the scope of the specification and following claims.

DETAILED DESCRIPTION OF THE PREFERRED EMBODIMENTS

Throughout the following description and drawings, like reference numbers/characters refer to like elements. It should be understood that, although specific exemplary embodiments are discussed herein there is no intent to limit the scope of present invention to such embodiments. To the contrary, it should be understood that the exemplary embodiments discussed herein are for illustrative purposes, and that modified and alternative embodiments may be implemented without departing from the scope of the present invention.

Figure 1:
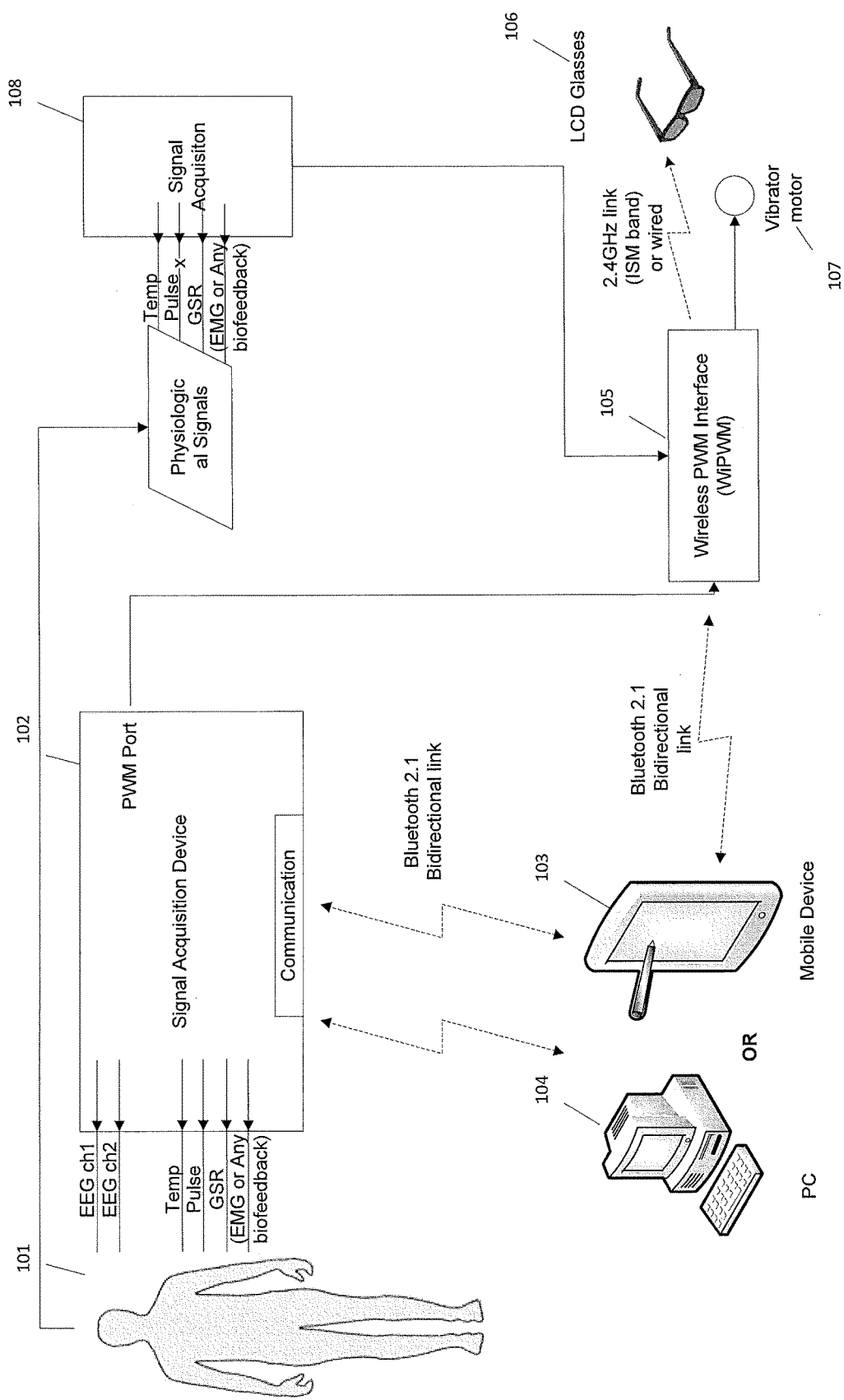
FIG. 1 is a block diagram of a biofeedback system constructed in accordance with the principles of an embodiment of the present invention.

FIG. 1 depicts a "software/hardware combination" implementation in which the user or subject (a live human) 101 is connected to at least one of a signal acquisition device 102 and a signal acquisition device 108 that acquires the physiologic signal or signals and processes the signals and supplies them to a control signal generator to generate a feedback control signal or signals.

In the illustrated example, the control signal generator is a pulse width modulation (PWM) or wireless pulse width modulation (WiPWM) device 105, the output of which includes control signal(s) that can be supplied directly to a tactile feedback device or wearable device. However, it will be appreciated that the control signal generator may use modulation techniques other than PWM. The difference between signal acquisition device 102 and signal acquisition device 108 is that signal acquisition device 102 is a self-contained off-the-shelf or proprietary physiologic signal acquisition device while signal acquisition device 108 is an interface circuit of the PWM control signal generator. In either case, the physiologic signals may be processed by computing device or processor such as a personal or notebook computer 104 or mobile device 103 that is connected to the signal acquisition device 102 or 108 by a wired or wireless connection. The wireless connection may, for example, be a Bluetooth connection. Additional software is added to the mobile device 103 or PC 104 to analyze the user's physiologic signals according to a programmed criterion (e.g., increase, decrease, or maintain) and produces a reward or penalty signal according to some predetermined algorithm for transmission to the PWM control signal generator (also referred to as wireless PWM interface or WiPWM) 105. In addition, the computer 104 or mobile device 103 may be wirelessly connected directly to the PWM control signal generator 105 by a wireless connection such as a Bluetooth connection.

As illustrated in FIG. 1 (as well as FIGS. 3 and 4), the feedback is provided through a wearable device and a tactile feedback device. The tactile feedback device is in the form of a vibration motor 107 while the wearable device, in which the control signal is used to inhibit or modulate perception of the user's environment, is illustrated as LCD glasses 106. Both the vibration motor and LCD glasses may be conventional devices, with the glasses being similar to those used to achieve a 3-D effect in video viewing and gaming applications.

The physiologic signals acquired by signal acquisition devices may be any physiologic signal conventionally used for biofeedback or neurofeedback, including electroencephalographs (EEGs), electrocardiograph (ECGs), electromyography (EMG), skin temperature, skin conductance, heart rate, and/or event-related potentials (ERPs). The sensors or measuring devices that generate the physiologic signals are conventional and not a part of the present invention, and therefore any such sensors or devices may be used.

Figure 2:
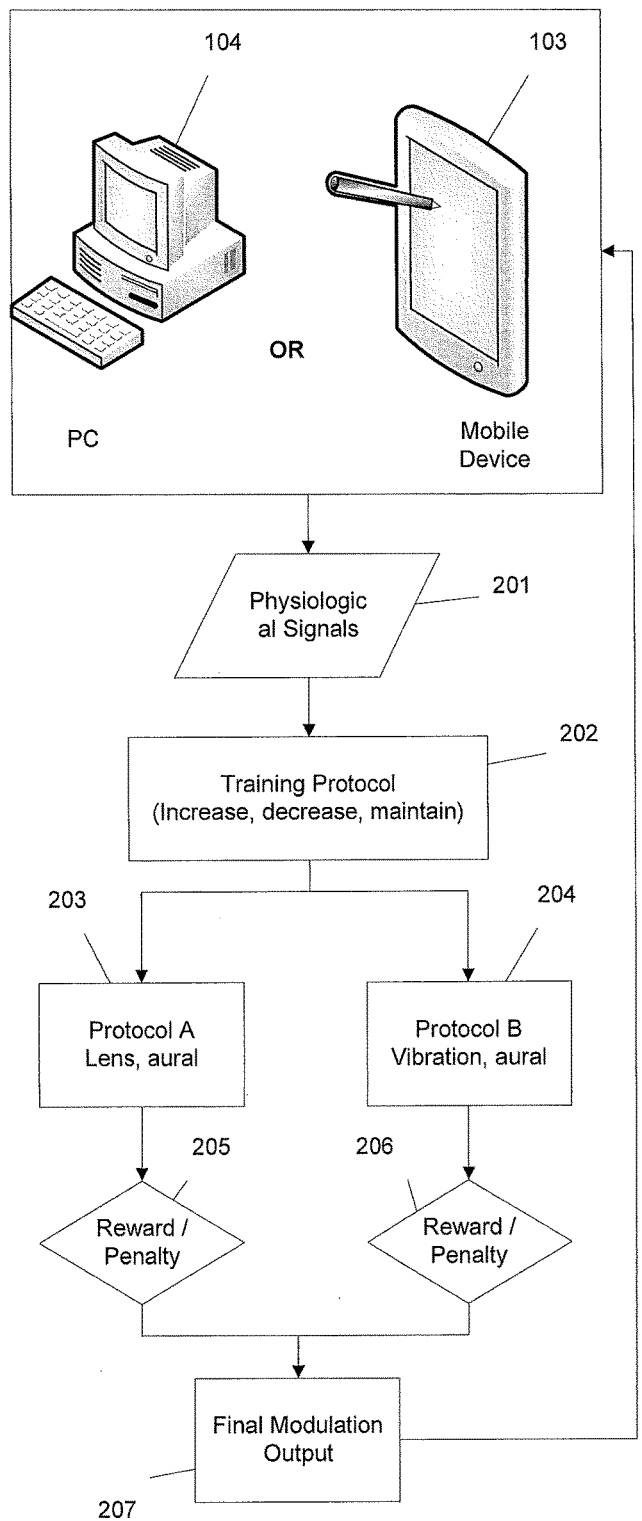
FIG. 2 is a flowchart of a software process method for implementing the system of FIG. 1

FIG. 2 depicts a software process in which the physiologic signals 201 are analyzed in a training protocol 202 according to a programmed criterion that results in the physiologic signals being either increased, decreased, or maintained. The process is then separated into a "Protocol A" subroutine 203 for determining a reward/penalty 205 to be applied to LCD glasses 106 of FIGS. 1, 3, and 4, and to a speaker according to the results of the training protocol, and a "Protocol B" subroutine 204 for determining a reward/penalty 206 to be applied to vibrator motor 107 and a speaker according to the results of the training protocol. The resulting "Protocol A" reward/penalty signal and "Protocol B" reward/penalty signal are then respectively modulated to obtain a final modulation output 207 that is output from mobile device 103 or PC 104 to the control signal generator (such as WiPWM 105 of FIG. 1), either directly or via the signal acquisition device 102, and ultimately applied to LCD glasses 106 and vibrator motor 107, the results being perceived by user or subject 101 in a closed loop feedback system.

According to the method of FIG. 2, a reward is produced if the physiologic signals match the criterion set forth by a training protocol. The criterion may be, by way of example and not limitation, increasing skin temperature, increasing the amplitude of a Beta2 (12-20 Hz) EEG, or a decrease in heart rate. The training protocol can include increasing one or more physiologic signals and/or decreasing one or more other physiologic signals, and may take the form of a training "ratio" protocol in which positive feedback is generated based on increasing the magnitude of certain physiologic signal or signals while at the same time also generating positive feedback based on decreasing the magnitude of another separate physiologic signal or signals.

An exemplary training ratio algorithm uses EEG bandwidths as the controlling physiologic signal to control a reward based on the magnitudes of the EEG bandwidths $[(f1+f2)/(f3+f4)]$, where f1, f2, f3, f4, are EEG bandwidths. According to this algorithm, if the magnitudes of f1 and/or f2 (on the numerator of the training ratio) increase, a reward is generated and if the magnitudes of f1 and/or f2 decrease or no longer increase, a penalty is generated. On the other hand, according to this algorithm, if the magnitudes of f3 and/or f4 (on the denominator of the training ratio) decrease, a reward is generated and if the magnitudes of f3 and/or f4 increase or are no longer decreasing, a penalty is generated.

When applied to eyeglasses 106, the reward may be that the lens becomes clearer, allowing the user to look through the lens to better see his or her environment, which is interpreted by the user as a reward for his or her physiologic signals meeting the programmed criterion. The visual reward may be complimented by an aural reward in the form of a positive and pleasing note or melody, a chime, a chord, a tone, or a tick, received by the user via an internal audio system and speaker of a mobile device, or via headphones worn by the user and connected to the mobile device. Conversely, a penalty may equate to the lens becoming darker or less clear, inhibiting the user from looking through the lens to see his or her environment. The penalty might also include the non-occurrence of a positive aural reward, and/or the occurrence of a negative aural penalty. The negative aural penalty might be a negative and displeasing noise such as a loud or high-pitch noise or chirp, a honk, a deep or low tone, or other displeasing sound audible to the human ear.

Alternatively, when applied to the vibration 107, the reward may equate to the non-occurrence of a tactile vibration (caused for example by a coin vibrator motor placed in a band and worn around the wrist or ankle of the user), and/or the non-occurrence of a negative aural penalty, while the penalty may equate to the occurrence of tactile vibration felt by the user and interpreted as a penalty for his or her physiologic signals not meeting the programmed criterion, and/or the presence of a negative aural award.

In another embodiment of the invention, the programmed criterion which generates the feedback may be composed of a static threshold or thresholds in which only a certain magnitude level of a specified physiologic signal triggers the reward or penalty. For example, in the example of EEG bandwidth as the physiologic signal, the threshold to produce a reward may be a Beta2 (12-20 Hz) of at least 15 uV.

In yet another embodiment, an adaptive feedback system may be employed in which thresholds for feedback or rewards and penalties are set dynamically by the software in computer/mobile device 103,104 and affected by user performance. In an adaptive feedback system, the feedback difficulty is in proportion to user performance, such that when user performance improves, thresholds for rewards are increased to make it more difficult for the subject to receive a reward, and such that when user performance declines, the thresholds for penalties are decreased to make it easier for the subject to receive a reward or to not receive a penalty.

One known type of adaptive feedback system that may be employed is a fuzzy logic feedback system. The fuzzy logic feedback system enables several input parameters, such as rate of change, deviation from expected level, and previously achieved performance, to be related to the output. In the following example, the fuzzy logic system implementation adapts the user feedback with performance:

The first input variable, rate of change (ROC), is the time derivative of physiologic inputs and is a measure of how fast the user can jump into the target pattern (or frequency range), i.e., how fast the user can cause changes of a predetermined magnitude in the physiologic inputs expressed in the frequency domain (for example by a Fast Fourier Transform (FFT). The time interval (dT) is selectable by the user, for example 30, 60, or 120 seconds, while the rate of change is preferably weighted differently at the beginning and end of sessions. The results are characterized according to fuzzy logic principles by "membership functions." Examples of membership functions for the rate of change variable are "Poor," "Medium," and "Good." The second input variable, deviation from expected level (DEL), as the name implies, measures how close to expectations the user is performing. A preferred method of calculating the deviation is to average the physiologic values over buffer size and calculate the difference between the average and the expected values (which are set by the user). DEL membership functions are "Below Poor," "Poor," "At Level," "Passed Level," and "Achieved." The third input variable is previously achieved performance (PAP). Previously achieved performance can be taken into account by, and also be affected by, the most recent performance and, similar to a rank, can be increased (rewarded) or decreased (penalized) based on how well the user is performing in their current session. PAP membership functions may include, but are not explicitly defined in this example as, "Poor," "Medium," and "Good."

The outputs of the fuzzy logic system implementation are related to the input variables by a set of rules. The whole system works as a closed loop feedback apparatus. Therefore, a primary output can be derived as a value between 0-100%, as well as a hardware representation of it in the form of a variable DC voltage or frequency that can applied to the control signal generator or PWM device. The primary output value may also be represented graphically in terms of output membership functions such as "Decrease A lot," "Decrease, No Change," "Increase," and "Increase A lot."

When applied to a software process such as the one shown in FIG. 2, the fuzzy logic system implementation applies an algorithm to the FFT frequency spectrum of a physiologic signal of interest, for example in the form of a discrete Fourier transform (DFT) block that provides magnitudes of the frequencies of interest, the magnitudes then being weighted based on either "Protocol A" or "Protocol B" training bandwidths. The fuzzy block as described above is then implemented using IF-THEN statements. The physiologic signal of interest may, for example, be an EEG signal.

It will be appreciated that the present invention is not limited to any particular proportional, fixed threshold, or adaptive method of generating control signals representative of rewards and penalties, and that the specific method will depend on desired results and the type of physiologic signal or signals. The fuzzy logic system implementation described above is one known type of biofeedback and/or neurofeedback that may be used with the wearable device(s) of the preferred embodiments, but the description herein is not intended to be limiting. Also, those skilled in the art will appreciate that any of these methods may be applied not only to the system illustrated in FIG. 1, but also to the systems illustrated in FIGS. 3 and 4, and more generally in FIGS. 7-9.

Examples of everyday activities to which the system of FIG. 1 and method of FIG. 2 may be applied include, but are not limited to, the following examples. In each of these examples, the reward for better performance and improved behavior includes the lightening of the lenses of the eyeglass 106, an increase in an audible tone, and a decrease in the vibration provided by motor 107. The penalty for poor performance includes a darkening of the lenses of the eyeglass 106, a decrease in the audible tone and an increase in vibration:

Driving—While either learning to drive or becoming a better driver using driving simulators, the method and system of the invention provides visual, auditory and tactile feedback of cognitive performance to include, but not limited to: when paying better attention to the task, the lenses of the eyeglass lighten, and there is an increase in the audible tone and a decrease of the vibration, when improving visual perception of distance to other objects, the lenses of the eyeglass lighten, and there is an increase in the audible tone and a decrease of the vibration; when there is a decrease in the impulsive responses to outside movement of things and other drivers, the lenses of the eyeglass lighten, and there is an increase of in the audible tone and a decrease of the vibration; when there is a reduction in the response time to the driving experience, the lenses of the eyeglass lighten, and there is an increase of in the audible tone and a decrease of the vibration.

Writing—While either typing on a keyboard or handwriting, the method and system of the invention provides visual, auditory and tactile feedback of cognitive performance to include but not limited to: when paying better attention to flow of sentence structure, the lenses of the eyeglass lighten, and there is an increase in the audible tone and a decrease of the vibration; when improving efficiency in grammatical and spelling accuracy, the lenses of the eyeglass lighten, and there is an increase in the audible tone and a decrease of the vibration; when transferring thought into the written word at a faster rate, the lenses of the eyeglass lighten, there is an increase in the audible tone and a decrease of the vibration: when less distracted in completing the written task and overall efficiency to the task, the lenses of the eyeglass lighten, and there is an increase of in the audible tone and a decrease of the vibration.

Reading—While reading, the method and system of the invention provides visual, auditory and tactile feedback of cognitive performance to include but not limited to; when the speed in which reading material is cognitively absorbed is increased, the lenses of the eyeglass lighten, and there is an increase in the audible tone and a decrease of the vibration; when recall and memory of reading material is increased, the lenses of the eyeglass lighten, and there is an increase in the audible tone and a decrease of the vibration; when there is improved accuracy in the processing of the read material and overall efficiency to the task, the lenses of the eyeglass lighten, and there is an increase in the audible tone and a decrease of the vibration.

Relaxing—While attempting to relax, the method and system of the invention provides visual, auditory and tactile feedback of the degree of relaxed mind and body state to include but not limited to: when able to reach a physical relaxed state at a faster rate, the lenses of the eyeglass lighten, and there is an increase in the audible tone and a decrease of the vibration; when there is a reduction in the amount of muscle tension throughout the body and in feelings of anxiety, the lenses of the eyeglass lighten, and there is an increase of in the audible tone and a decrease of the vibration: and when there is a reduction in mind racing and a meditating state, the lenses of the eyeglass lighten, and there is an increase in the audible tone and a decrease of the vibration.

Watching television and/or any visual medium—While attempting to watch visual medium, the method and system of the invention provides visual, auditory and tactile feedback of cognitive performance to include but not limited to: when there is increased attention to the task, the lenses of the eyeglass lighten, and there is an increase in the audible tone and a decrease of the vibration; when an improvement in memory and recall of the observed information occurs, the lenses of the eyeglass lighten, and there is an increase in the audible tone and a decrease of the vibration; and when ability to connect the discreet portions of the content together in a meaningful way improves, the lenses of the eyeglass lighten, and there is an increase in the audible tone and a decrease of the vibration.

Figure 3:
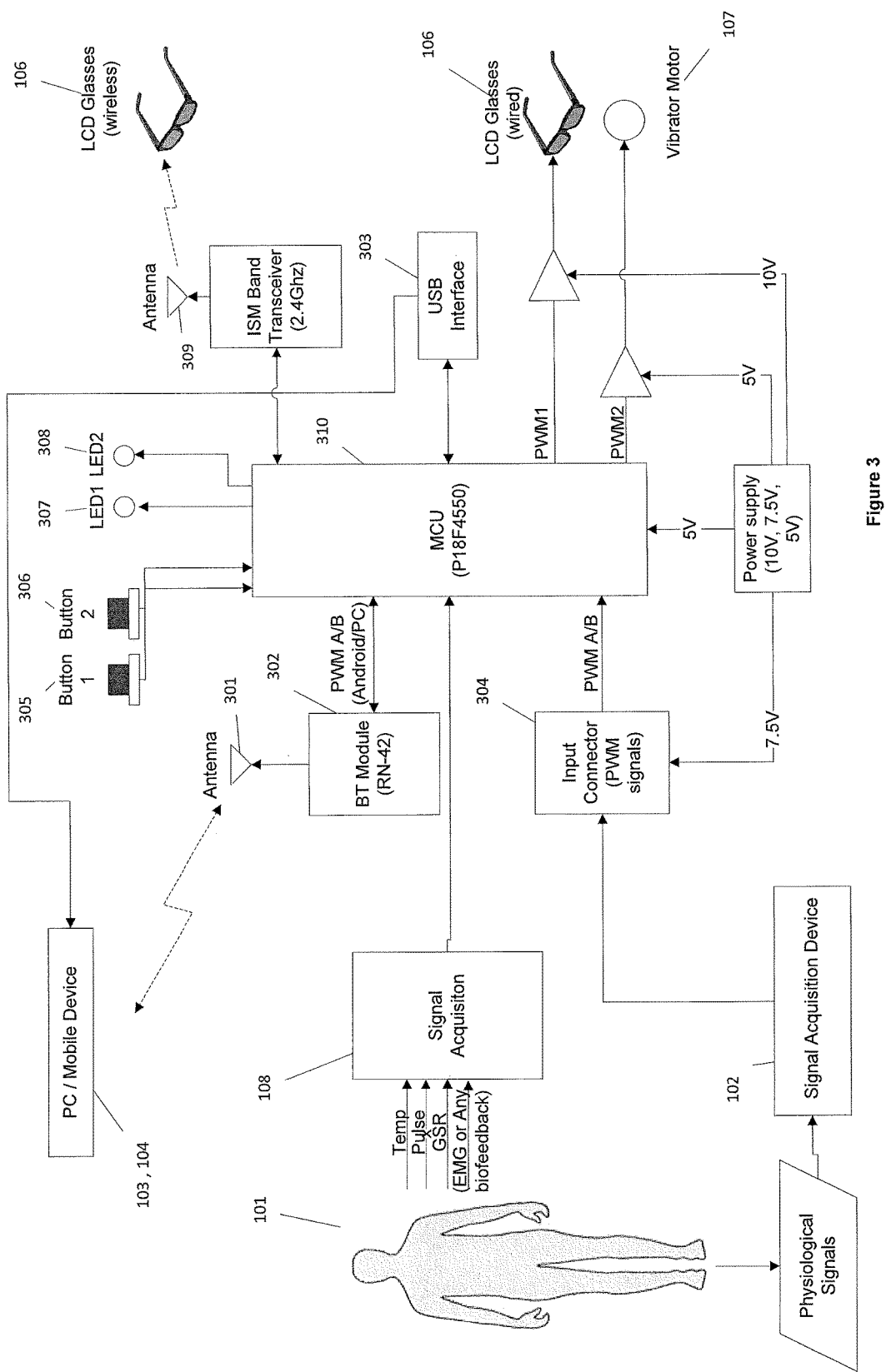
FIG. 3 is a block diagram of a biofeedback system as illustrated in FIG. 1, showing details of a particular hardware implementation of the wireless PWM interface module.
Figure 5:
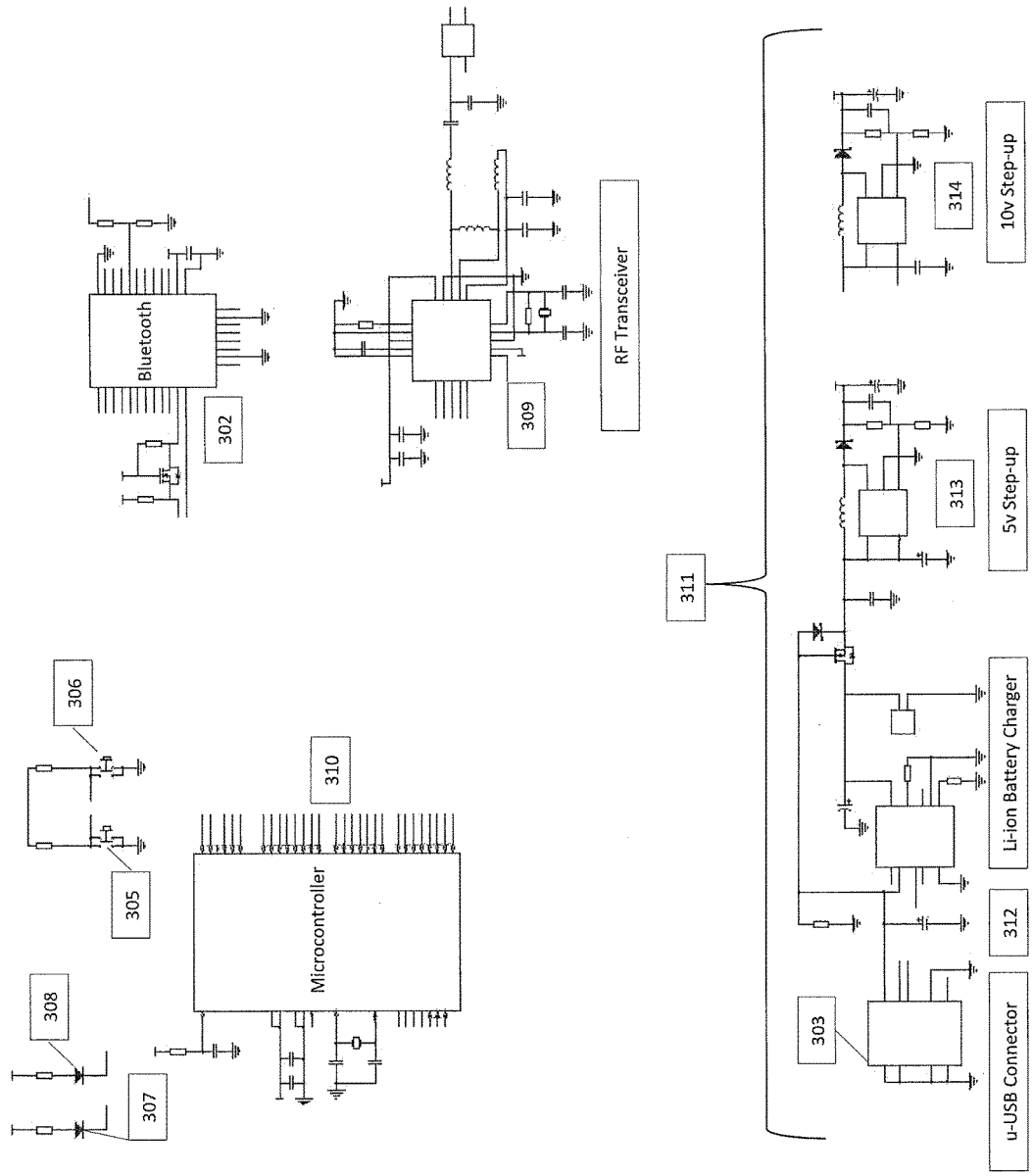
FIG. 5 is a schematic circuit diagram of an exemplary implementation of the wireless PWM interface module of FIG. 3.

FIG. 3 shows a version of the system of FIG. 1, in which the WiPWM block is replaced by discrete blocks 301-310 that together correspond to the wireless PWM interface 105 of FIG. 1. Further details of a particular non-limiting implementation of the wireless PWM interface are shown in FIG. 5, with correspondence between functional blocks and more detailed hardware schematics being indicated by like reference numerals, although the functional blocks of FIG. 3 are not limited to the particular hardware illustrated in FIG. 5.

As illustrated in FIG. 3, the physiologic signals measured from user or subject 101 are received by signal acquisition device 108 of the WiPWM module and sent to computer 104 or mobile device 103 for processing in software depicted in FIG. 2 and described above. The reward/penalty signal is received from computer 104 or mobile device 103 through an antenna 301 and Bluetooth module 302 connected to MCU (or micro-controller) 310, or through a USB interface 303 connected to the MCU 310. MCU 310 may, by way of example and not limitation may be a Microchip Technologies PIC18F4550 microcontroller as shown in more detail in FIG. 5.

Referring still to FIG. 3, subject 101 could alternatively be connected to signal acquisition device 102 rather than WiPWM signal acquisition 108, in which case the reward/penalty signal could come from signal acquisition device 102 through wires connected to an input connector 304 and then into MCU 310. It is also possible for MCU 310 to receive reward/penalty signals directly from PC/Mobile Device 103, 104 via a USB Interface 303. A power supply 311 is illustrated in FIG. 5 as including a lithium-ion battery charger 312, and respective 5V and 10V step-up circuits 313 and 314.

Referring again to FIG. 3, the reward/penalty signals received by MCU 310 are subject to tuning by the user or subject 101 (or any other person such as a clinician) via Button1 305 and Button2 306. Button1 305 and Button2 306 are connected to the MCU 310 and enable the feedback intensity to be turned up and down by the user. In addition, light emitting diodes LED1 307 and LED2 308 or other displays or indicators may be provided to give other information about the feedback to the user. Finally, MCU 310 then sends the corresponding reward/penalty signal to antenna 309 for wireless transmission to LCD glasses 106, or directly to the glasses 106 via a wired connection, and/or sends a corresponding reward/penalty signal to the vibration motor 107 via the illustrated wired connection, or via a wireless connection (not shown).

Figure 4A:
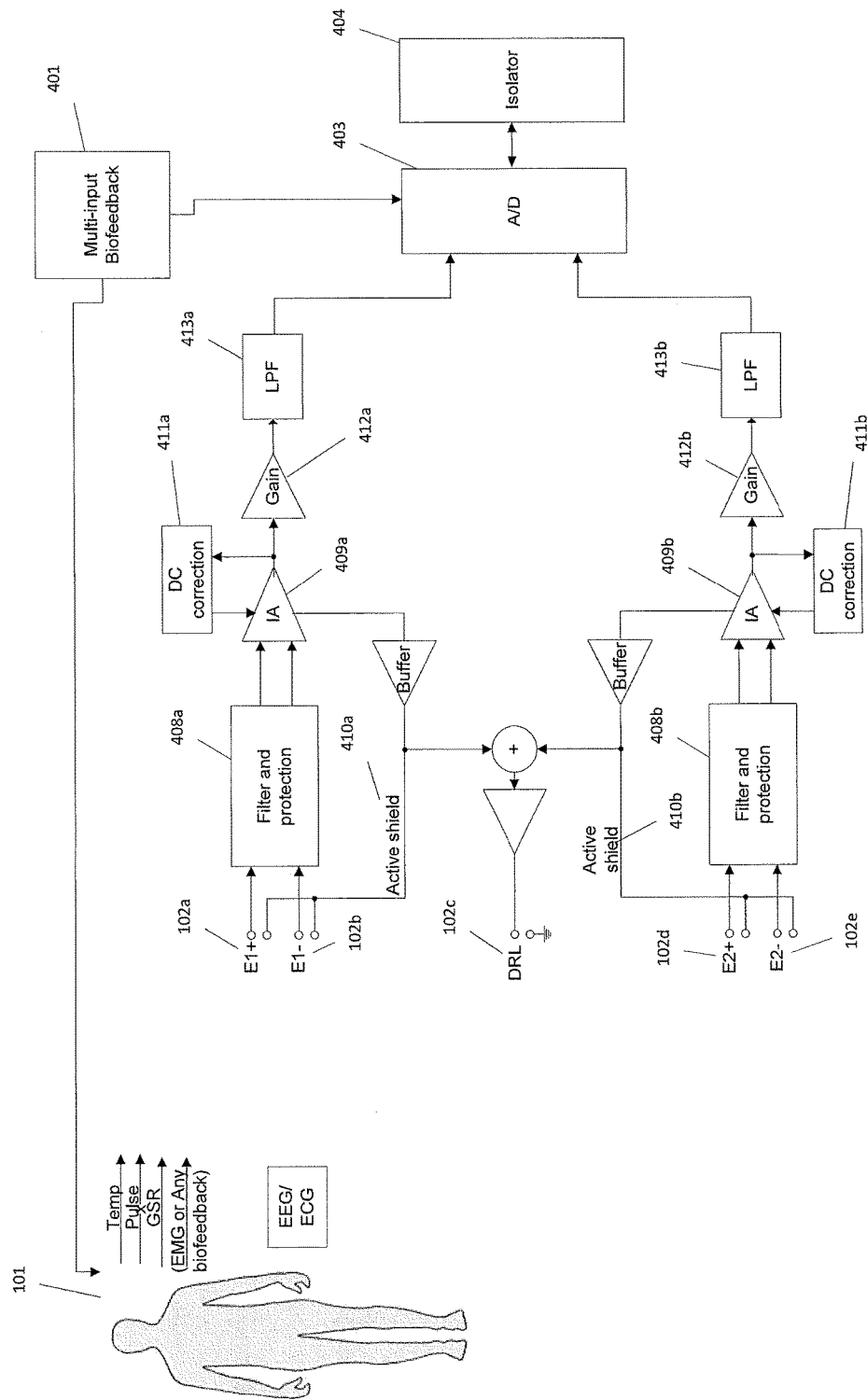
FIGS. 4A and 4B are block diagrams of a biofeedback system as illustrated in FIG. 1, showing details of a particular hardware implementation of the signal acquisition module.
Figure 4B:
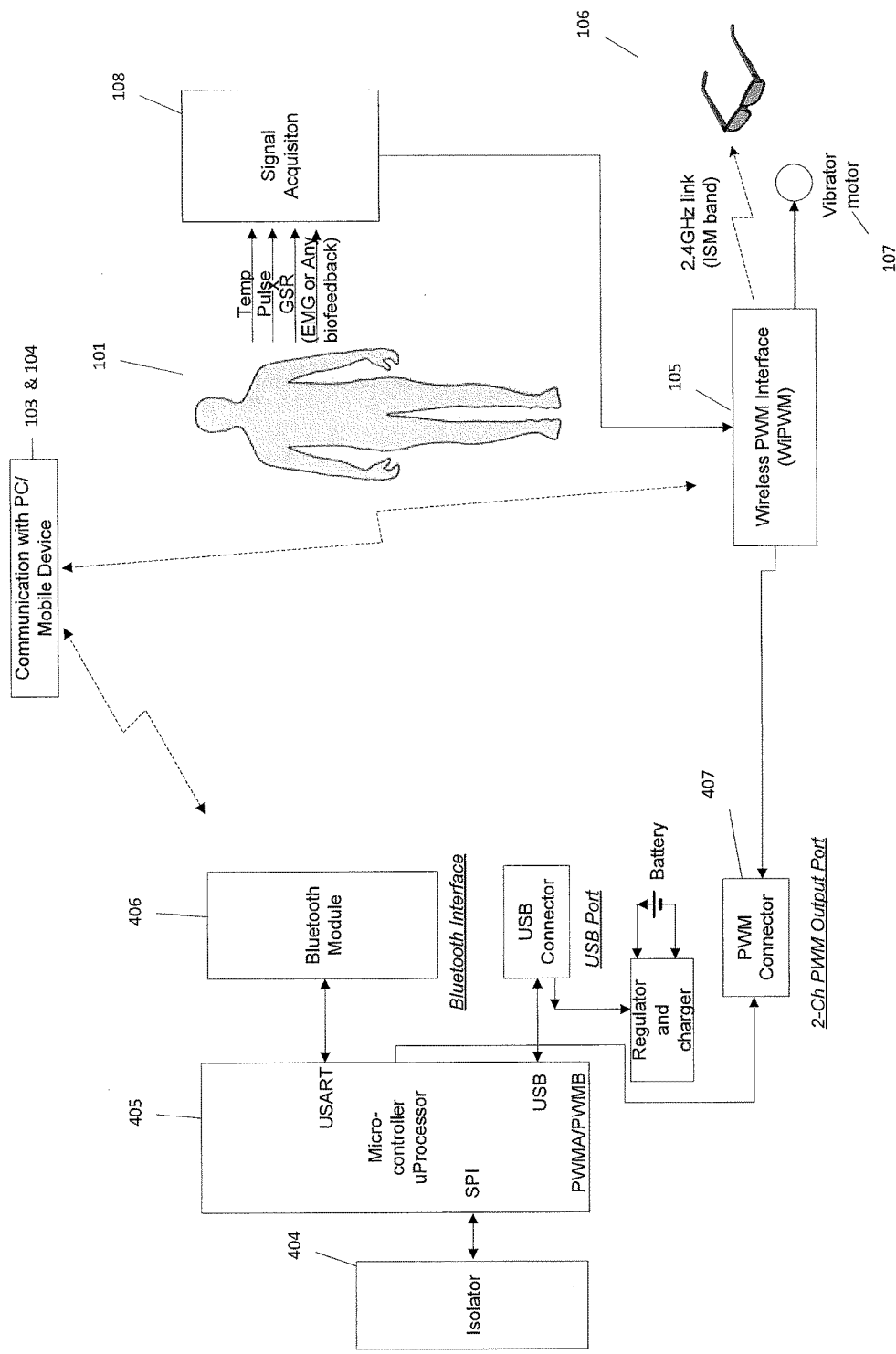

Referring now to FIGS. 4A and 4B, which shows a detailed construction of the signal acquisition device 102 of FIG. 1, the user or subject 101 is connected to the signal acquisition device and the physiologic data (e.g., EEG/ECG data) collected by electrodes (not shown) attached to the user or subject 101 is received by sensor inputs that may include, as illustrated, a first active sensor input 102a (channel 1), a reference sensor input 102b (channel 1), a driven right leg grounding sensor input 102c, a second active sensor input 102d (channel 2), and a second reference sensor input 102e (channel 2). Further details of a particular non-limiting implementation of the signal acquisition device are shown in FIG. 6, with correspondence between functional blocks and more detailed hardware schematics being indicated by like reference numerals, although the functional blocks of FIGS. 4A and 4B are not limited to the particular hardware illustrated in FIG. 6.

Those skilled in the art will appreciate that the specific signal acquisition circuitry described and illustrated herein is exemplary only, and that the circuitry through which the physiologic signals are fed and the corresponding signal process may be varied in numerous ways without departing from the scope of the invention. In particular, although the accompanying drawings illustrate circuitry that is particularly adapted to acquire brainwave (EEG) signals that indicate subject index of attention or focus according to the above-described training protocol, the circuitry may be modified to acquire other types of physiologic signals and/or for compatibility with other feedback protocols.

Figure 6:
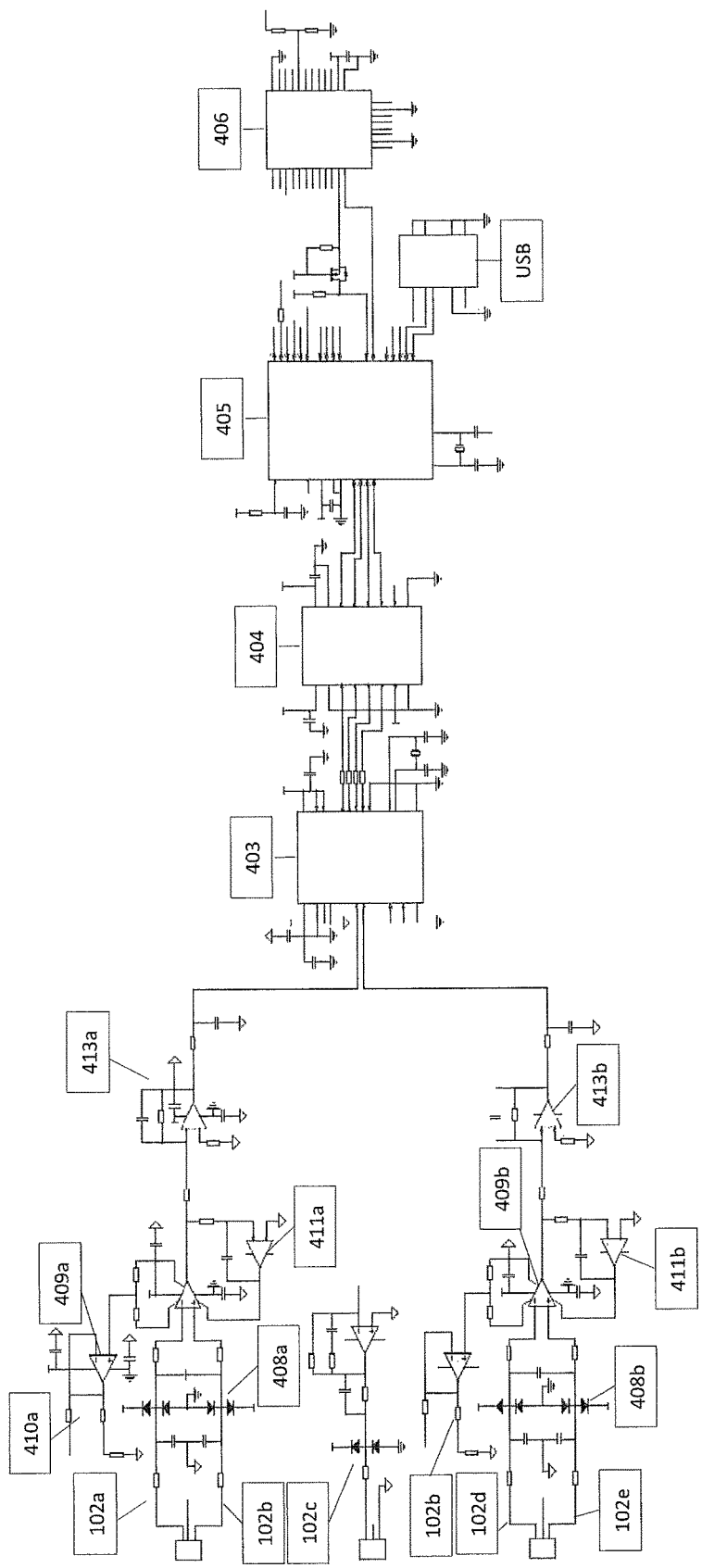
FIG. 6 is a schematic circuit diagram of a particular hardware implementation of the signal acquisition module of FIGS. 4A and 4B.

In the examples illustrated in FIGS. 4 and 6, the signal acquisition device 102 is designed to pick up low amplitude brainwave signals (on the order of a few micro-volts) received on two independent channels through the sensor inputs 102a, 102b, 102c, 102d, 102e, and then amplify, digitize and transmit them over a BLUETOOTH™ wireless communications link, or other communications link, to the mobile device 103 or computer 104. Due to low level of the signals received from EEG electrodes respectively connected to sensor inputs 102a, 102b, 102c, 102d, 102e, and the likely presence of strong background noise and interference, the amplifier must have a high CMRR (Common Mode Rejection Ratio) as well as noise suppression capabilities. This is achieved by utilizing a high-CMRR/ultra-low-noise instrumentation amplifier at the input stage. Further filtering and bandwidth control is handled in the next stages.

Preferably, in order to achieve the best performance at input frequencies as low as 0.2 Hz (per specifications), a quasi-DC approach is implemented. Therefore, the amplifier is DC-coupled to eliminate the need for very large DC blocking capacitors while limiting the minimum input frequency to 0.2 Hz. The amplifier also utilizes a mechanism to compensate for the effect of skin resistance changes and DC offsets and drifts usually created by a change in the static potentials created between the contact point of electrodes and the skin, as well as the DC offset drift of the input stage. This feature is achieved using a DC correction servo loop inside the amplifier.

Still referring to FIGS. 4 and 6, the respective channel 1 and channel 2 sensor inputs are connected to input filter and protection circuit 408a for channel 1 and 408b for channel 2, which forms a first input stage. Inputs are clamped to VCC and −VCC in order to protect against high voltage spikes and static electricity. Capacitor clamps have also been utilized to short any high frequency spike at the inputs. The input and protection circuits 408a and 408b are respectively connected to instrumentation amplifiers (IAs) 409a for channel 1 and 409b for channel 2, which are preferably low-noise low-CMRR instrumentation amplifiers with a gain set to, for example, ~12.5. The IAs amplify the differential signals receives on their (+IN) and (−IN) inputs, thus resulting in suppression of the common mode signals which are present on both inputs. Active shields 410a (for channel 1) and 410b (for channel 2) are achieved by injecting part of the input signal to the shield of the input cables. The effect is to cancel interference pick up on the shield conductor and thus improving signal to noise ratio.

As illustrated in FIGS. 4 and 6, the average value of the input signals from both channels is buffered and fed-back to the subject via the DRL connection 102c. DRL 102c effectively cancels hum and noise picked up by the subject's body, which acts as a receiving antenna for the interference. The DRL connection 102c is also protected from static discharge using clamping diodes.

In the circuitry of FIGS. 4 and 6, the above-mentioned DC correction servo loops 4111a for channel 1 and 4111b for channel 2 are each composed of an integrator (with fc at, for example, 0.1 Hz) that adjusts the DC offset of the instrumentation amplifier by monitoring the DC content at the output of the IAs 409a and 409b. The purpose is to keep the DC content as close to ground level (zero volts) of the amplifier as possible. This also prevents the next stages from being saturated by high DC offset. For this purpose, respective gain stages 412a for channel 1 and 412b for channel 2 are required to bring the signal level to a level close to the full-scale input level of the analog-to-digital or A/D converter (ADC). This is required to make the best use of the maximum resolution of the ADC. Each gain stage is also equipped with a low pass second order filter loop (with Fc set at, for example, 250 Hz). Finally, another low pass filter 413a for channel 1 and 413b for channel 2 is added before feeding the amplified signal to the ADC. This stage also limits the output current of the gain stage and thus acts as a protection circuit. The −3 dB point of the filter is set at, for example, ~1600 Hz.

Referring still to FIGS. 4 and 6, the A/D converter 403 of the illustrated embodiment is a very low noise, two-channel, 24-bit analog-to-digital converter available from Texas Instruments, Inc., with sampling rates reaching 30K samples per second (sps). The A/D converter must be initialized for proper operation by the microprocessor. There is a programmable gain stage in the A/D converter that is set to operate at a gain of 2. The sampling rate of the A/D converter is also limited to 2,000 sps to make the best use of the anti-aliasing filter of the converter. The ADC 403 is preferably connected to an isolator 404 so as to achieve a high level of electrical isolation between the output of the signal acquisition device, which may include a USB connector, and the input stages that connect directly to subject's body. This helps to improve the safety of the amplifier as well as provide better signal-to-noise performance due to isolation of the digital part from the analog part.

As illustrated in FIGS. 4A and 4B, the user or subject 101 may alternatively or additionally be connected to multi input biofeedback circuitry 401, which contains provisions for accepting a multitude of physiologic signals including but not limited to EMG, EEG, ECG, galvanic skin response (GSR), skin temperature, heart rate, pulse oximeter, breathing rate and depth, or any other physiologic signal related to the subject. Details of such circuitry will be known to those skilled in the art of biofeedback.

As illustrated, micro-controller or microprocessor 405, and the firmware programmed into it, handle all the tasks of initializing and acquiring data as well as constructing data packets to be sent over Bluetooth or a USB connection to the host computer 104 or mobile device 103. As shown in FIG. 6, an example of a suitable microcontroller 405 is again the Microchip Technologies PIC18F4550 44-Pin, high-performance, enhanced flash, USB microcontrollers, although other microcontrollers or microprocessors may be substituted, as will be understood by those skilled in the art. The transmission of the packets and handshaking mechanism with the host is carried on based on a set of commands/responses defined in the communication protocol. The micro-controller 405 also handles the power saving strategy on a regular basis. All peripherals (e.g., A/D 403, isolator 404, and BLUETOOTH™ (BT) module 406) are set into sleep mode to reduce power consumption when not in use. The micro-controller 405 automatically enters into an idle mode based on the current status of the amplifier and certain operational flags. Two PWM outputs are also generated by the micro-controller that can be used to interface with external devices such as wireless PWM interface 105 via a hard-wired connection, for example through a PWM connector 407.

Referring still to FIGS. 4A and 4B, data acquired from the A/D converter is packed and transmitted by the microcontroller 405 to the host mobile device 103 or computer 104 via the BLUETOOTH™ (BT) module 406 or USB connector (USB). The BLUETOOTH™ module 406 must be initialized by the microcontroller 405 for proper operation. This is done at power-up when parameters such as the transmission power of the BLUETOOTH™ module 406 are also adjusted. The BLUETOOTH™ module 406 and/or USB connector also receives commands from the host computer 104 or mobile device 103 and passes them to the microcontroller 405. Among these commands are those related to setting the PWM outputs as well as start/stop commands that trigger relevant actions by the signal acquisition device 102. If the BLUETOOTH™ link is detected to be inactive for more than 60 seconds, the BLUETOOTH™ module 406 is taken to sleep mode to reduce power consumption.

Those skilled in the art will appreciate that the invention is not limited to a particular communications protocol or packet architecture. However, for the example where the physiologic signals are EEG signals, a suitable packet architecture and communications protocol (based on the EEG Bluetooth Communications Protocol, Rev. 2, April, 2013) are as follows:

Downlink packets are received from the EEG amplifier and consist of 7 bytes. Data is received MSB-first, the first 3 bytes (B0, B1, B2) representing channel 1, the second 3 bytes (B3, B4, B5) channel 2, and the last byte (B0) represents the status byte, as indicated in the following table:

| B0 | B1 | B2 | B3 | B4 | B5 | B6 |
|---|---|---|---|---|---|---|
| CH1 | CH1 [15:8] | CH1 [7:0] | CH2 [23:16] | CH2 [15:8] | CH2 [7:0] | STATUS |

Uplink packets consist of 2 bytes that are sent to EEG amplifier as follows:

| B0 | B1 |
|---|---|
| COMMAND | PARAMETER |

The 24-bit data of each channel when completely received, represents a 2's complement value, the positive full-scale value is represented by 7FFFFFh, while the negative full-scale value is 800000h.

A status byte is received as the last byte of the downlink packet, representing the status of the EEG amplifier. The status information is packed as follows:

| b7 | b6 | b5 | b4 | b3 | b2 | b1 | b0 |
|---|---|---|---|---|---|---|---|
| FAULT | SOFT | RSV3 | RSV2 | RSV1 | BAT2 | BAT1 | BAT0 | wherein b7 is the hardware status (1=Hardware fault and 0=No fault); b6 is the software status (1=Running (packets contain valid channel data) and 0=Idle (no channel data)); b5 is a calibration status (1=Calibrating and 0=Calibration done); b4 and b3 are reserved); and b2 to b0 indicate battery status (111=battery full, 011=battery charging, and 000=battery low, with intermediate states of b2:b0 representing corresponding values of battery voltage, between low (minimum) to high (maximum)).

Commands are transmitted in uplink to the EEG amplifier. Exemplary commands are indicated in the following table.

Some commands may have parameters which must be sent in the second byte of the packet, otherwise zero must be transmitted in the parameter field.

| Description | Command (hex) | Parameter |
| --- | --- | --- |
| START | 20 h | 0 |
| ACK | 21 h | 0 |
| STOP | 40 h | 0 |
| SET ADC GAIN | 21 h | Gain (1 h, 2 h, 4 h, 10 h, 20 h, 40 h) |
| LOOP BACK | 22 h | ON (1), OFF (0) |
| SET SAMPLE RATE | 24 h | Sample rate (0 h-FFh) |
| SET PWM-A | 28 h | PWM value (0 h-FFh) |
| SET PWM-B | 29 h | PWM value (0 h-FFh) |
| OFFSET0 (offset byte 0) | 30 h | OFC0 |
| OFFSET1 (offset byte 1) | 31 h | OFC1 |
| OFFSET2 (offset byte 2) | 32 h | OFC2 |
| SLEEP | 80 h | 0 |
| WAKEUP | 81 h | 0 |
| SOFT RESET | AAh | 55 h |

Figure 7:
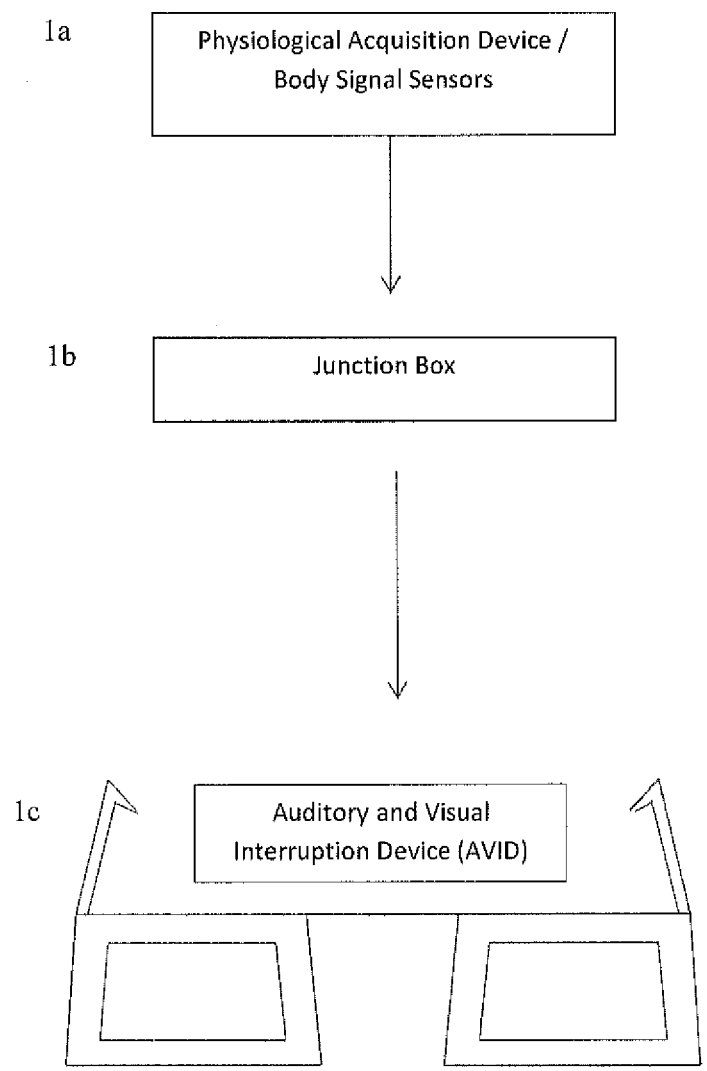
FIGS. 7-9 are diagrams illustrating general principles of the biofeedback system of the present invention.
Figure 8:
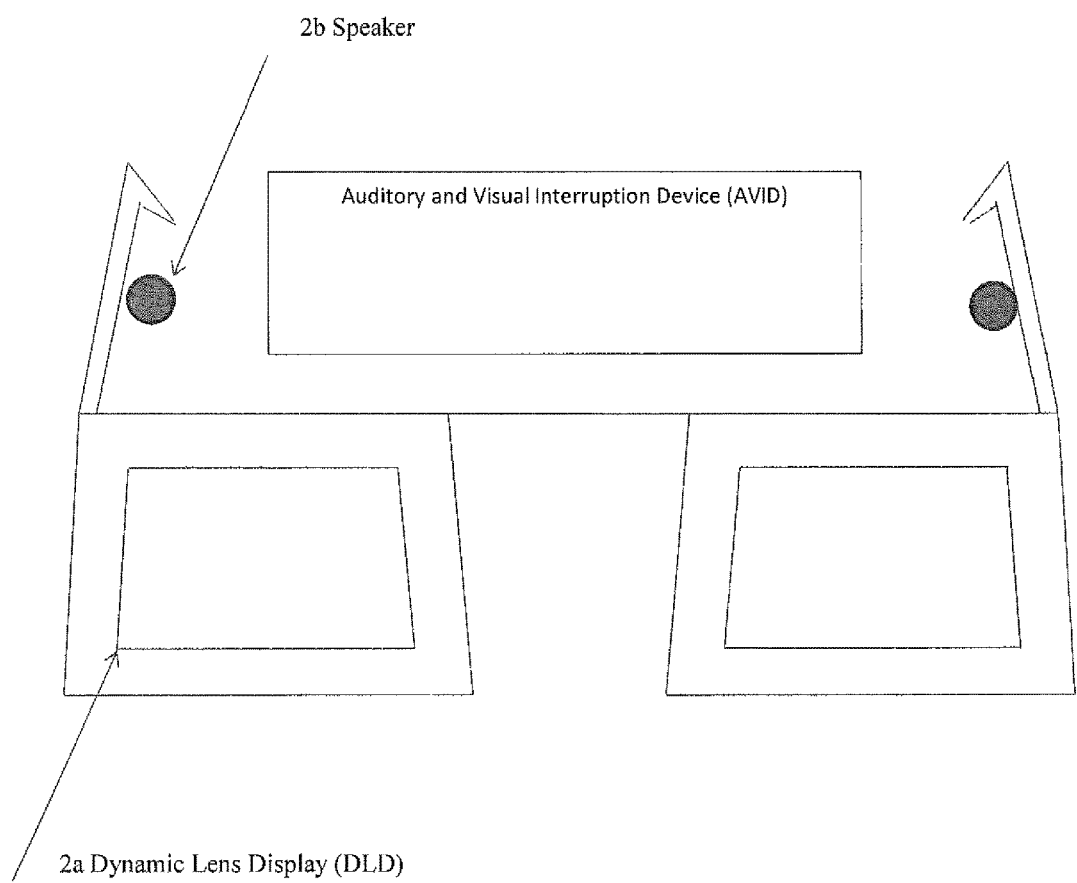
Figure 9:
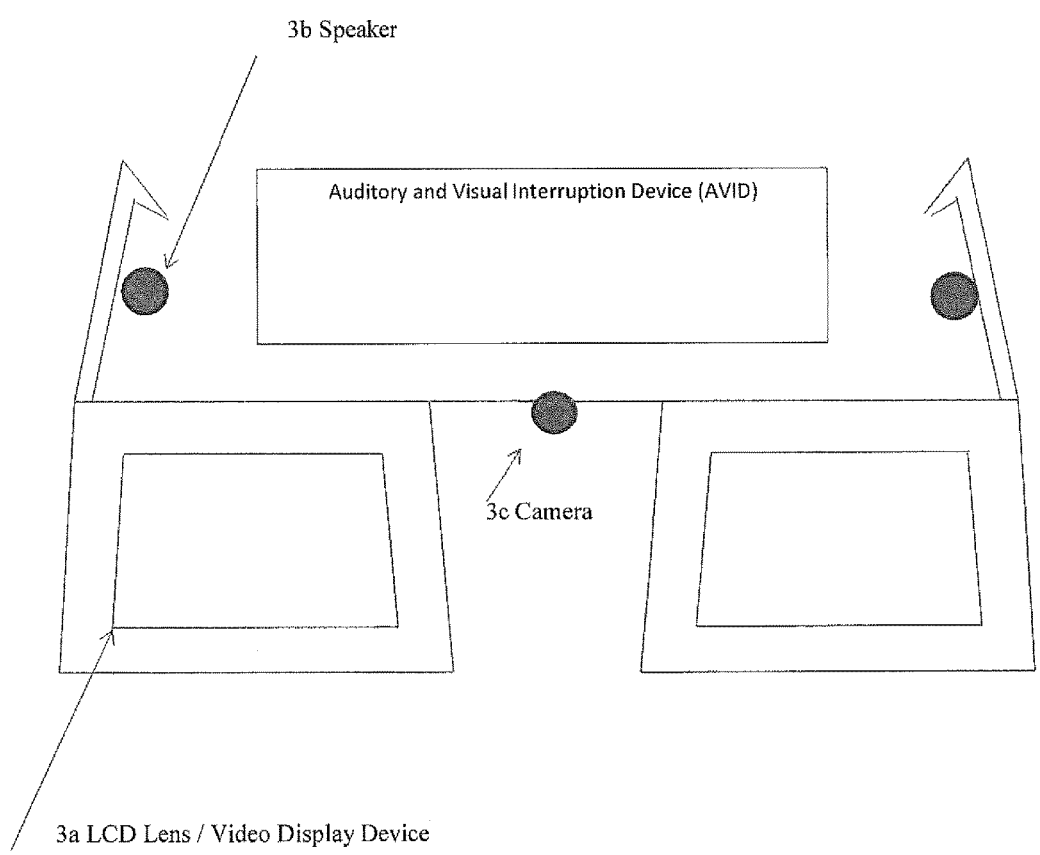

FIGS. 7-9 are schematic illustrations of more general principles of the preferred embodiments of FIGS. 1-6. In particular, FIG. 7 shows the overall feedback loop provided by the invention, which allows the invention to be used during real-life tasks. The feedback loop includes a physiologic acquisition device 1a made up of sensors or electrodes that measure, by way of example and not limitation, EEGs, ECGs, EMG, skin temperature, skin conductance, heart rate, and/or event-related potentials (ERPs), and any associated electronics, cables, or communications devices. If EEG data is collected, the EEG data may include, is not limited to, EEG data such as sensory motor rhythm (SMR), delta waves, theta waves, alpha waves, beta waves, and gamma waves.

The feedback loop also includes a junction box 1b, which includes all necessary physiologic signal processing, analyzing and calculating, and control signal generating components, such as the ones illustrated in FIG. 1. Finally, the feedback loop includes a wearable device 1c, referred to as an "audio video interruption device" (AVID), although it is to be understood that the audio component is optional or may take other forms, such as a headset, and that "video" may be replaced by any sensory input that can be modulated or inhibited by control signals from the junction box (in the embodiments of FIGS. 1-6, for example, the AVID may instead take the form of an eyeglass with a dynamic lens display or LCD that controls transmission of light and/or a wearable vibration motor, with an optional separate speaker).

FIG. 8, for example, shows an AVID with a dynamic lens display 2a and a speakers 2b on the earpieces, while FIG. 9 shows an AVID 3a with an LCD lens 3a, speakers 3b, and a camera 3c for supplying images of the environment through the LCD lens and to which the feedback control signals are applied to modify the images of the environment. The speakers 2b and 3b may include conventional speakers, ear buds, headphones, tactile vibration bone transducers, and any other device for producing aural stimuli. The aural stimuli may include, in addition to those described above, harmonics, tones, chords, binaural beats, up-ticks, down-ticks, warble tones, variable tones, variable pitch, or any other auditory feedback, as well modulation of external environmental sounds. Other aural stimuli may include the modulation of sound perceived by the user from the external environment by way of a microphone capturing the sound from the user's external environment and headphones worn by the user which block natural sound from the external environment (which could be noise-cancelling circuitry or other physical blockage of sound waves) and a system to modulate the amount of sound that is passed through to the headphones worn by user based on the performance of the users physiologic signals. Still further, the means for changing visual perception of the external environment may include not only a dynamic video display or LCD lens, but also heads-up displays, retinal projection, video projection, or any other means of producing visual context, and the means for modulating, inhibiting, or altering perception of the environment may include, in addition to means for modulating brightness or clarity of images passing through the wearable device directly from the environment, means for removing, moving, creating, duplicating, or otherwise changing an entire scene or certain aspects of a scene reproduced on a video display present in at least a part of the field of view of the user or subject. It will be appreciated that numerous other such modifications and variations of the illustrated embodiments are possible, and it is therefore intended that the invention be limited solely in accordance with the appended claims.

What is claimed is:

1. A biofeedback system that enables biofeedback training to be accomplished during interaction by an individual with the individual's environment, comprising:
    a physiologic data acquisition device for acquiring physiologic data concerning the individual;
    a processor connected to the physiologic data acquisition device for processing said physiologic data and generating at least one control signal in response to said processing of the physiologic data;
    a wearable device through which the individual receives sensory information that includes, at least, visual information from the individual's environment, said wearable device comprising a lens display arranged to interrupt the visual information and thereby change the individual's visual perception of the individual's environment by varying a clarity or opacity of the lens display in response to said at least one control signal.

2. A biofeedback system as claimed in claim 1, wherein said wearable device is an eyeglass device, said eyeglass device including said lens display.

3. A biofeedback system as claimed in claim 2, wherein the lens display includes a liquid crystal which blocks light passing through the lens when electrified.

4. A biofeedback system as claimed in claim 3, wherein the lens is arranged to be electrified at varying intensities to produce different levels of opacity.

5. A biofeedback system as claimed in claim 2, wherein said physiologic signals include one or more of the following physiologic signals: electroencephalographs (EEGs), electrocardiograph (ECGs), electromyography (EMG), skin temperature, skin conductance, heart rate, and/or event-related potentials (ERPs).

6. A biofeedback system as claimed in claim 2, wherein said control signal causes said said clarity or opacity to be varied in a way that constitutes a reward if the physiologic signals match a criterion set forth by a training protocol.

7. A biofeedback system as claimed in claim 6, wherein the training protocol includes analysis of the physiologic data to determine whether one or more physiologic signals has increased and/or decreased, and in which the reward is generated based on the increase and/or decrease in the magnitude of at least one said physiologic signals.

8. A biofeedback system as claimed in claim 2, wherein said physiologic signals include an electroencephalograph (EEG) to indicate an individual's mental engagement at a task, and said control signal is generated based on a bandwidth of the EEG.

9. A biofeedback system as claimed in claim 8, wherein said clarity or opacity is varied as a function of a ratio $[(f1+f2)/(f3+f4)]$ of four respective EEG bandwidths, where f1, f2, f3, f4, are the respective EEG bandwidths.

10. A biofeedback system as claimed in claim 2, wherein said clarity or opacity is varied based on comparison of said physiologic data with a fixed threshold.

11. A biofeedback system as claimed in claim 2, wherein said clarity or opacity is varied based on comparison of said physiologic data with an adaptive threshold.

12. A biofeedback system as claimed in claim 11, wherein said adaptive threshold is determined by fuzzy logic.

13. A biofeedback system as claimed in claim 2, further comprising a complemental feedback device including an auditory feedback device and/or a tactile feedback device for respectively conveying auditory and tactile feedback to the individual in response to at least one said control signal.

14. A biofeedback system as claimed in claim 2, further comprising a complemental feedback device including a tactile feedback device for conveying tactile feedback to the individual in response to at least one said control signal, wherein said tactile feedback device includes a vibrating mechanism for transmitting vibrations to the individual in response to the control signal.

15. A biofeedback system as claimed in claim 2, further comprising a complemental feedback device including an auditory feedback device for conveying auditory feedback to the individual in response to at least one said control signal, wherein said auditory feedback device includes a speaker or headphone for generating a pleasant sound that serves as an aural reward or an unpleasant sound that serves as a penalty or negative aural reward.

16. A biofeedback system as claimed in claim 1, wherein said physiologic signals include one or more of the following physiologic signals: electroencephalographs (EEGs), electrocardiograph (ECGs), electromyography (EMG), skin temperature, skin conductance, heart rate, and/or event-related potentials (ERPs).

17. A biofeedback system as claimed in claim 1, wherein said control signal causes said sensory information to be modulated in a way that constitutes a reward if the physiologic signals match a criterion set forth by a training protocol.

18. A biofeedback system as claimed in claim 17, wherein the training protocol includes analysis of the physiologic data to determine whether one or more physiologic signals has increased and/or decreased, and in which the reward is generated based on the increase and/or decrease in the magnitude of at least one said physiologic signals.

19. A biofeedback system as claimed in claim 1, wherein said physiologic signals include an electroencephalograph (EEG) to indicate an individual's mental engagement at a task, and said control signal is generated based on a bandwidth of the EEG.

20. A biofeedback system as claimed in claim 19, wherein said sensory information is modulated as a function of a ratio $[(f1+f2)/(f3+f4)]$ of four respective EEG bandwidths, where f1, f2, f3, f4, are the respective EEG bandwidths.

21. A biofeedback system as claimed in claim 19, wherein said sensory information is modulated based on comparison of said physiologic data with a fixed threshold.

22. A biofeedback system as claimed in claim 19, wherein said sensory information is modulated based on comparison of said physiologic data with an adaptive threshold.

23. A biofeedback system as claimed in claim 22, wherein said adaptive threshold is determined by fuzzy logic.

24. A biofeedback system as claimed in claim 1, further comprising an auditory feedback device and/or a tactile feedback device for respectively conveying auditory and tactile feedback to the individual in response to at least one said control signal.

25. A biofeedback system as claimed in claim 1, further comprising a complemental feedback device including a tactile feedback device for conveying tactile feedback to the individual in response to at least one said control signal, wherein said tactile feedback device includes a vibrating mechanism for transmitting vibrations to the individual in response to the control signal.

26. A biofeedback system as claimed in claim 1, further comprising a complemental feedback device including an auditory feedback device for conveying auditory feedback to the individual in response to at least one said control signal, wherein said auditory feedback device includes a speaker or headphone for generating a pleasant sound that serves as an aural reward or an unpleasant sound that serves as a penalty or negative aural reward.

27. A biofeedback system that enables biofeedback training to be accomplished during interaction by an individual with the individual's environment, comprising:
   a physiologic data acquisition device for acquiring physiologic data concerning the individual;
   a processor connected to the physiologic data acquisition device for processing said physiologic data and generating at least one control signal in response to said processing of the physiologic data;
   a wearable device through which the individual receives sensory information from the individual's environment, said wearable device being arranged to interrupt or modify the sensory information received by the individual in response to said at least one control signal,
   wherein said wearable device is an eyeglass device, said eyeglass device including a dynamic lens display, and said control signal being supplied to said dynamic lens display to modulate visual information received through said eyeglass device, and
   wherein said physiologic data is EEG data, analysis of said physiologic data is carried out in the frequency domain and transformed physiologic data is processed according to three input variables: rate of change, deviation from expected level, and previously achieved performance.

28. A biofeedback system that enables biofeedback training to be accomplished during interaction by an individual with the individual's environment, comprising:
   a physiologic data acquisition device for acquiring physiologic data concerning the individual;
   a processor connected to the physiologic data acquisition device for processing said physiologic data and generating at least one control signal in response to said processing of the physiologic data;
   a wearable device through which the individual receives sensory information from the individual's environment, said wearable device being arranged to interrupt or modify the sensory information received by the individual in response to said at least one control signal,
   wherein said physiologic data is EEG data to indicate an individual's mental engagement at a task, and
   wherein analysis of said physiologic data is carried out in the frequency domain and the transformed physiologic data is processed according to three input variables:

rate of change, deviation from expected level, and previously achieved performance.

29. A biofeedback method that enables biofeedback training to be accomplished during interaction by an individual with the individual's environment, comprising the steps of:
providing the individual with a wearable device through which the individual receives sensory information from the individual's environment, the wearable device comprising a lens display;
acquiring physiologic data concerning the individual;
using a processor to process the physiologic data and generate at least one control signal in response to said processing of the physiologic data;
interrupting visual information received by the individual through the wearable device to change the individual's visual perception of the individual's environment by varying a clarity or opacity of the lens display in response to said at least one control signal.

30. A biofeedback method as claimed in claim 29, wherein said wearable device is an eyeglass device, said eyeglass device including said lens display, wherein the clarity or opacity of the lens display is varied by controlling an amount of light passing through a liquid crystal in the lens display.

31. A biofeedback method as claimed in claim 30, wherein the step of acquiring physiologic signals include the step of measuring one or more of the following physiologic signals: electroencephalographs (EEGs), electrocardiograph (ECGs), electromyography (EMG), skin temperature, skin conductance, heart rate, and/or event-related potentials (ERPs).

32. A biofeedback method as claimed in claim 30, wherein said step of varying a clarity or opacity of the lens display is carried out in a way that constitutes a reward if the physiologic signals match a criterion set forth by a training protocol.

33. A biofeedback method as claimed in claim 32, wherein the training protocol includes analysis of the physiologic data to determine whether one or more physiologic signals has increased and/or decreased, and in which the reward is generated based on the increase and/or decrease in the magnitude of at least one said physiologic signals.

34. A biofeedback method as claimed in claim 30, wherein said physiologic signals include an electroencephalograph (EEG) to indicate an individual's mental engagement at a task, and said control signal is generated based on a bandwidth of the EEG.

35. A biofeedback method as claimed in claim 34, wherein said clarity or opacity of the lens display is varied as a function of a ratio $[(f1+f2)/(f3+f4)]$ of four respective EEG bandwidths, where f1, f2, f3, f4, are the respective EEG bandwidths.

36. A biofeedback method as claimed in claim 30, wherein said clarity or opacity of the lens display is varied based on comparison of said physiologic data with a fixed threshold.

37. A biofeedback method as claimed in claim 30, wherein said clarity or opacity of the lens display is varied based on comparison of said physiologic data with an adaptive threshold.

38. A biofeedback method as claimed in claim 37, wherein said adaptive threshold is determined by fuzzy logic.

39. A biofeedback method as claimed in claim 29, further comprising the step of providing auditory feedback and/or tactile feedback for respectively conveying auditory and tactile feedback to the individual in response to at least one said control signal.

40. A biofeedback method as claimed in claim 39, wherein the step of providing auditory feedback and/or tactile feedback comprises the step of transmitting vibrations to the individual in response to the control signal.

41. A biofeedback method as claimed in claim 39, wherein the step of providing auditory feedback and/or tactile feedback comprises the step of generating a pleasant sound that serves as an aural reward or an unpleasant sound that serves as a penalty or negative aural reward.

42. A biofeedback method as claimed in claim 29, wherein the step of acquiring physiologic signals include the step of measuring one or more of the following physiologic signals: electroencephalographs (EEGs), electrocardiograph (ECGs), electromyography (EMG), skin temperature, skin conductance, heart rate, and/or event-related potentials (ERPs).

43. A biofeedback method as claimed in claim 29, wherein said step of modulating said sensory information comprises the step of modulating the sensory information in a way that constitutes a reward if the physiologic signals match a criterion set forth by a training protocol.

44. A biofeedback method as claimed in claim 43, wherein the training protocol includes analysis of the physiologic data to determine whether one or more physiologic signals has increased and/or decreased, and in which the reward is generated based on the increase and/or decrease in the magnitude of at least one said physiologic signals.

45. A biofeedback method as claimed in claim 29, wherein said physiologic signals include an electroencephalograph (EEG) to indicate an individual's mental engagement at a task, and said control signal is generated based on a bandwidth of the EEG.

46. A biofeedback method as claimed in claim 45, wherein said visual information is modulated as a function of a ratio $[(f1+f2)/(f3+f4)]$ of four respective EEG bandwidths, where f1, f2, f3, f4, are the respective EEG bandwidths.

47. A biofeedback method as claimed in claim 29, wherein said visual information is modulated based on comparison of said physiologic data with a fixed threshold.

48. A biofeedback method as claimed in claim 47, wherein said visual information is modulated based on comparison of said physiologic data with an adaptive threshold.

49. A biofeedback method as claimed in claim 48, wherein said adaptive threshold is determined by fuzzy logic.

50. A biofeedback method that enables biofeedback training to be accomplished during interaction by an individual with the individual's environment comprising the steps of:
acquiring physiologic data concerning the individual;
using a processor to process the physiologic data and generate at least one control signal in response to said processing of the physiologic data;
interrupting or modifying sensory information received by the individual through a wearable device in response to said at least one control signal,
wherein said wearable device is an eyeglass device, said eyeglass device including a dynamic lens display, and said control signal being supplied to said dynamic lens display to modulate visual information received through said eyeglass device, and
wherein said physiologic data is EEG data, analysis of said physiologic data is carried out in the frequency domain and the transformed physiologic data is processed according to three input variables: rate of change, deviation from expected level, and previously achieved performance.

51. A biofeedback method that enables biofeedback training to be accomplished during interaction by an individual with the individual's environment, comprising the steps of:
  acquiring physiologic data concerning the individual;
  using a processor to process the physiologic data and generate at least one control signal in response to said processing of the physiologic data;
  interrupting or modifying visual information received by the individual through a wearable device in response to said at least one control signal, and
  wherein said physiologic data is EEG data, analysis of said physiologic data is carried out in the frequency domain and the transformed physiologic data is processed according to three input variables: rate of change, deviation from expected level, and previously achieved performance.

* * * * *